United States Patent [19]

Owen et al.

[11] 4,265,825

[45] May 5, 1981

[54] PROCESS FOR THE PREPARATION OF N-(HALOALKYL)SULFONAMIDE

[75] Inventors: Peter W. Owen; Zita K. Harmon; Donald A. Tomalia, all of Midland, Mich.

[73] Assignee: The Dow Chemical Company, Midland, Mich.

[21] Appl. No.: 76,111

[22] Filed: Sep. 17, 1979

[51] Int. Cl.$^3$ .............................................. C07C 143/72
[52] U.S. Cl. ...................................... 260/401; 564/91; 564/98
[58] Field of Search ............. 260/556 A, 556 AR, 401

[56] References Cited

U.S. PATENT DOCUMENTS 4,120,804 10/1978 Smith et al. .......................... 252/47.5

OTHER PUBLICATIONS

R. H. Wiley et al.; Chemical Reviews, vol. 44, pp. 468–469 (1949).

Primary Examiner—Jacqueline V. Howard
Attorney, Agent, or Firm—Michael L. Glenn

[57] ABSTRACT

N-(haloalkyl)sulfonamides represented by the formula

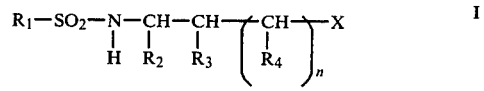

wherein $R_1$ is a $C_1$–$C_{20}$ aryl, alkaryl, aralkyl or alkyl group; $R_2$, $R_3$ and $R_4$ are each independently hydrogen or methyl groups; n is the integer 0 or 1 and X is a chloro, bromo or iodo group, are prepared by reacting an N-(haloalkyl)sulfonyl imide with a $C_1$–$C_6$ alkanol.

8 Claims, No Drawings

PROCESS FOR THE PREPARATION OF N-(HALOALKYL)SULFONAMIDE

BACKGROUND OF THE INVENTION

This invention relates to a novel process for preparing an N-(haloalkyl)sulfonamide by the reaction of an N-(haloalkyl)sulfonyl imide with an alcohol.

N-(2-haloethyl)sulfonamide is useful as a chemical intermediate in the preparation of herbicides (see, for example, U.S. Pat. No. 3,205,253), photographic intermediates and other useful compositions. It is known in the art to prepare an N-(2-haloethyl)sulfonamide by the reaction of an alkane or arylene sulfonyl halide with ethylenimine. However, the toxicity of ethylenimine has reduced the utility of this prior art process. Therefore, an alternative route to this chemical intermediate is desirable.

SUMMARY OF THE INVENTION

A novel process has now been discovered for preparing N-(haloalkyl)sulfonamides represented by the formula

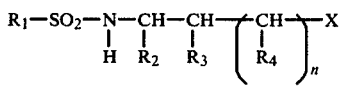  I which comprises reacting an N-(haloalkyl)sulfonyl imide represented by the formula

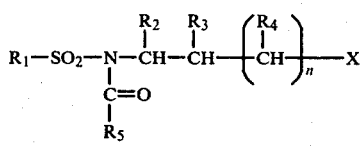  II with a $C_1$–$C_6$ alkanol, so as to prepare the N-(haloalkyl)sulfonamide; wherein, at each occurrence, $R_1$ is $C_1$–$C_{20}$ alkyl, alkaryl, aralkyl or aryl; $R_5$ is hydrogen, $C_1$–$C_{20}$ alkyl, alkaryl, aralkyl or aryl; $R_2$–$R_4$ are each independently hydrogen or methyl; n is the integer 0 or 1 and X is a chloro, bromo or iodo group.

DETAILED DESCRIPTION OF THE INVENTION

N-(Haloalkyl)Sulfonyl Imide Reactant

The N-(haloalkyl)sulfonyl imide reactant is conveniently prepared by reacting a 2-oxazoline or 2-oxazine represented by the formula

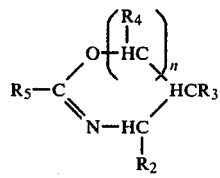  III with a sulfonyl halide represented by the formula $R_1SO_2X$  IV wherein $R_1$–$R_5$, n and X have the aforesaid identities.

The reactant represented by formula III is preferably a 2-oxazoline, i.e., n is 0. $R_2$–$R_4$ are each preferably hydrogen. $R_5$ is preferably phenyl, methyl or ethyl, with ethyl being the most preferred. The sulfonyl halide represented by formula IV is preferably a benzene, methane, dodecylbenzene or ethane sulfonyl halide, most preferably a benzene sulfonyl halide. X is preferably a chloro group.

The reaction between the 2-oxazoline or 2-oxazine and the sulfonyl halide can be conducted in the presence or absence of solvents or diluents, but is conveniently conducted in a liquid phase. Any organic compound which is substantially inert in the reaction is suitable as a diluent; however, some diluents, such as perchloroethylene, adversely affect the yield of the sulfonyl imide. Representative compounds preferred as diluents include chloroform, methylene chloride, toluene and benzene.

The manner in which the oxazoline or oxazine reactant is brought together with the sulfonyl halide can affect the yield of the N-(haloalkyl)sulfonyl imide intermediate. Desirably, the oxazoline is added to the sulfonyl halide, inasmuch as the reverse order of addition produces initially a substantially molar excess of the oxazoline. Desirably, the oxazoline or oxazine reactant and the sulfonyl halide are reacted in a mole ratio in the range from about 1:1 to about 1:3, preferably in substantially equimolar quantities. A substantial molar excess of an oxazoline reactant produces a polymer, as is taught in U.S. Pat. No. 4,120,804.

The rate of addition of the oxazoline or oxazine is desirably relative slow, as rapid rates of addition produce substantial amounts of products of side reactions. The optimal rate of addition of the oxazoline or oxazine is not susceptible to quantitative expression, because of its interdependence with other factors, such as, reaction temperature and concentration of reactants.

The temperature during the reaction of the oxazoline or oxazine with the sulfonyl halide is desirably in the range from about 0° C. to about 120° C., preferably from about 20° C. to about 100° C. At reaction temperatures above and below the aforementioned desirable range, substantial quantities of the products of side reactions result. Times required for substantially complete reaction depend upon the reaction temperature and the specific reactants, but times from 1 to 8 hours are typical.

Alcoholysis of Sulfonyl Imide

The reaction between the sulfonyl imide reactant and the alcohol is conveniently conducted by introducing the alcohol directly into the medium resulting from the preparation of the sulfonyl imide. However, it is operable but less desirable to first isolate the sulfonyl imide and then react it in the liquid phase with the alcohol. Desirably, the alcohol reactant and the sulfonyl imide are reacted in a mole ratio in the range from about 1:1 to about 50:1. The rate at which the alcohol is brought together with the sulfonyl imide is not critical.

The alcohol reactant is a $C_1$–$C_6$ alkanol. The alcohol is preferably a primary or secondary $C_1$–$C_4$ alkanol or mixture thereof, most preferably methanol or ethanol. The alcohol reactant and liquid reaction medium are preferably substantially anhydrous to prevent the hydrolysis of the intermediates and the desired sulfonamide product to undesirable by-products. A small, but catalytic amount of an alkali metal salt of the alcohol reactant is advantageously present to effect greater yields of the sulfonamide product. The alkali metal alkoxide is desirably present in a quantity from about 0 to about 5 mole percent of the sulfonyl imide reactant.

The temperature during the reaction of the alcohol and the sulfonamide is desirably in the range from about 0° to about 150° C., preferably about 20° to about 130° C. Conveniently, the temperature of the reaction medium is maintained so as to cause refluxing of the alcohol. Times required for substantially complete reaction depend upon the reaction temperature and the specific reactants and ratios, but times from about 5 to about 30 hours are typical.

The reaction can be conducted in a batchwise or continuous process.

Utility of N-(Haloalkyl)Sulfonamide

The halo group borne by the sulfonamide can be displaced by a variety of nucleophiles known to those skilled in the art to thereby produce compositions useful as herbicides, as photographic intermediates or in other end uses. The N-(3-halopropyl)sulfonamide and N-(2-haloethyl)sulfonamide possess analogous properties, which render them interchangeable in some end uses.

The N-(2-haloethyl)sulfonamides can be readily converted in the presence of caustic or other bases (e.g., sodium carbonate, potassium carbonate, sodium methoxide and the like) to the corresponding aziridine. Therefore, this method can be used to prepare aziridines without the use of ethylenimine. The aziridine can be readily ring-opened with hydrogen halides and other acids.

The following examples are illustrative of the present invention and are not to be construed as limiting the scope thereof in any manner. All parts and percentages are by weight unless otherwise specified.

EXAMPLE 1

A solution of 45.34 grams (0.457 mole) of 2-ethyl-2-oxazoline in 20 milliliters (ml) of chloroform is added dropwise over a period of 2 hours to a stirred charge of 85.11 grams (0.482 mole) of benzene sulfonyl chloride at an initial temperature of 25° C. The resulting exothermic reaction increases the reaction temperature to 59° C. The reaction mixture is then heated at 80° C. for 15 hours. Analysis of this intermediate by proton magnetic resonance spectroscopy determines that 100 percent of the 2-ethyl-2-oxazoline was converted and that the N-(2-chloroethyl)-N-propionyl-N-benzene sulfonyl imide is present in 95 percent yield.

To the aforementioned reaction mixture is added 90 ml (4.86 moles) of anhydrous methanol. The mixture is refluxed for 10 hours. The volatile components, such as methanol, chloroform and methyl propionate, are then removed by distillation at reduced pressure. The resulting 104.2 grams solid crystalline residue is found by proton magnetic resonance spectroscopy to consist of about 60 percent N-(2-chloroethyl)-benzene sulfonamide. The crude product is recrystallized once in carbon tetrachloride to yield a substantially pure product having a melting point of from 62° C. to 65° C.

EXAMPLE 2

A solution of 39.6 grams (0.40 mole) of 2-ethyl-2-oxazoline in 75 ml of methylene chloride is added dropwise over a period of 40 minutes to a stirred solution of 45.8 grams (0.40 mole) of methane sulfonyl chloride in 5 ml of methylene chloride at an initial temperature of 25° C. The resulting exothermic reaction increases the reaction temperature to 37° C. The methylene chloride is distilled from the reaction mixture at reduced pressure to leave 83.7 grams of a pale yellow liquid. This liquid is determined by proton magnetic resonance analysis to contain N-(2-chloroethyl)-N-propionyl-N-methane sulfonyl imide in 90 percent purity.

To the aforementioned reaction mixture is added 75 ml (1.875 moles) of anhydrous methanol. The mixture is refluxed for 13 hours and the volatile components are removed by distillation at reduced pressure. The residue after distillation is 32.0 grams of a pale yellow liquid. This residue is identified by proton magnetic resonance to consist of about 60 percent N-(2-chloroethyl)-methane sulfonamide.

What is claimed is:

1. A process for preparing N-(haloalkyl)sulfonamides represented by the formula

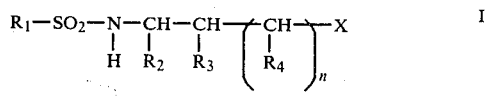

which comprises reacting an N-(haloalkyl)sulfonyl imide represented by the formula

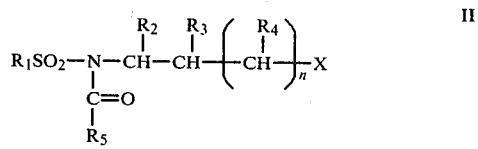

with a $C_1$–$C_6$ alkanol, so as to prepare the N-(haloalkyl)sulfonamide, wherein, at each occurrence, $R_1$ is aryl, alkaryl, aralkyl or alkyl having up to 20 carbon atoms; $R_2$–$R_4$ are each independently hydrogen or methyl; $R_5$ is hydrogen, aryl, alkaryl, aralkyl or alkyl having up to 20 carbon atoms; n is the integer 0 or 1 and X is chloro, bromo or iodo.

2. The process described in claim 1 wherein $R_1$ is methyl, ethyl, dodecylphenyl or phenyl and $R_5$ is methyl, ethyl or phenyl.

3. The process described in claim 2 wherein n is the integer 0.

4. The process described in claim 3 wherein $R_2$–$R_4$ each is hydrogen.

5. The process described in claim 4 wherein $R_5$ is ethyl and X is chloro.

6. The process described in claim 2 wherein the N-(haloalkyl)sulfonimide is prepared by reacting a 2-oxazoline or 2-oxazine represented by the formula

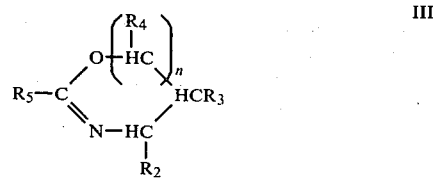

with a sulfonyl halide represented by the formula $R_1SO_2X$  IV.

7. The process described in claim 6 wherein the 2-oxazoline and the sulfonyl halide are reacted in step (a) in a mole ratio from about 1:1 to about 1:3 at a reaction temperature in the range from about 0° C. to about 120° C.

8. The process described in claim 7 wherein the alcohol and the N-(2-haloethyl)sulfonyl imide are reacted in a mole ratio in the range from about 1:1 to about 50:1 at a reaction temperature in the range from about 20° C. to about 130° C.

* * * * *